United States Patent [19]

Mori

[11] Patent Number: 4,966,450
[45] Date of Patent: Oct. 30, 1990

[54] LIGHT RADIATION STAND

[76] Inventor: Kei Mori, 3-16-3-501, Kaminoge, Setagaya-ku, Tokyo, Japan

[21] Appl. No.: 335,170

[22] Filed: Apr. 6, 1989

[30] Foreign Application Priority Data

Jul. 1, 1988 [JP] Japan .................................. 63-87849

[51] Int. Cl.⁵ ....................... G02B 7/18; G02B 11/04; F21V 21/14; A61N 5/06
[52] U.S. Cl. .................................... 350/603; 350/639; 248/474; 128/22; 128/397; 362/32; 362/139
[58] Field of Search ............... 350/603, 631, 632, 639, 350/96.1; 248/469, 474; 128/22, 397, 398; 362/32, 138, 139, 140, 141, 142

[56] References Cited

U.S. PATENT DOCUMENTS

| | | | |
|---|---|---|---|
| 1,897,281 | 2/1933 | Spampinato | 362/142 |
| 2,428,975 | 10/1947 | Lamb | 362/138 |
| 4,234,910 | 11/1980 | Price | 362/32 |
| 4,843,530 | 6/1989 | Mori et al. | 362/32 |

Primary Examiner—Jon W. Henry
Attorney, Agent, or Firm—Jordan and Hamburg

[57] ABSTRACT

(1) A light radiation stand for holding a light emitting end of a light-transmitting fiber optic cable is described. The light radiation stand comprises a stand base, one or more deformable flexible conduits vertically installed on the upper part of the base, a fiber optic cable holding means mounted on the tip end portion of each conduit and a mirror integrally mounted to the base.

9 Claims, 12 Drawing Sheets

LIGHT RADIATION STAND

BACKGROUND OF THE INVENTION

The present invention relates to a light radiation stand and, more particularly, to a stand being capable of radiating light rays transmitted through a fiber optic cable in any desired direction.

In recent years, a large number of persons suffer from hardly curable diseases such as gout, neuralgia and rheumatism, or pain from injury scars, bone fracture scars or from ill-defined diseases. Furthermore, no one can be free from skin aging which progresses gradually from a comparatively Young age. On the other hand, the present applicant has previously proposed to focus the sunlight or artificial light rays by the use of lenses or the like, to guide the same into a fiber optic cable and to transmit them to any place where the light is needed for illumination or for other purposes, for instance, to cultivate indoors plants, chlorella, fish or the like. In the process of research, it has been found that the visible light not containing ultraviolet and infrared rays is effective not only to promote the health of persons and prevent people's skin from aging by increasing a living body activity but also to noticeably aid in healing gout, neuralgia, bedsores, rheumatism, burn scars, skin diseases, injury soars, bone fracture scars and so on and in reliving the pain from such diseases. And further, on the basis of the above-mentioned inventor's discovery, the applicant has previously proposed a light radiation device for irradiating with the visible light not containing harmful-to-people ultraviolet and infrared rays with an aim of using it for healing various kinds of diseases, making beauty treatments and promoting the health of a person.

A light radiation device for use in medical treatments as previously proposed by the present applicant, comprises a fiber optic cable for receiving sunlight or artificial light at its input end and transmitting the light therethrough, a hood member installed at the light-emitting end portion of the fiber optic cable and a chair for a patient. The light to be transmitted through the fiber optic cable is one that corresponds to visible-spectrum light obtainable in various ways previously proposed by the present applicant. At the time of medical treatment, a patient is placed in the chair and the visible-spectrum light thus transmitted through the fiber optic cable is radiated onto the diseased part of a patient. As mentioned above, the light to be radiated onto the diseased part of the patient is the one that corresponds to the visible-spectrum components of the sunlight and free from the harmful elements such as ultraviolet and infrared raYs. Consequently, it may be possible to give medical treatment safely with no fear of exposuring a patient to harmful ultraviolet and infrared rays. However, the above-mentioned light radiation device has such drawbacks that it is too large and too expensive to be used in a family setting.

SUMMARY OF THE INVENTION

It is an object of the present invention to provide a light ray radiation stand capable of radiating the light rays transmitted through an optical conductor cable in an optional desired direction.

It is another object of the present invention to provide a light radiation stand which is suitably used in home for radiating the light transmitted through a fiber optic cable.

It is another object of the present invention to provide a light ray radiation stand which is low-cost; which is capable of being easily transported around; which doesn't need much space, and which can radiate the light rays in an optional desired direction and thereby can be used very readily.

It is another object of the present invention to provide a light radiation device, which is compact and very easy to operate, allowing for observing radiating state by means of a mirror and, furthermore, to preset bY the timer a irradiating period required in accordance with the state of disease, light intensity and other conditions concerned.

DESCRIPTION OF THE FREFERRED EMBODIMENTS

Figure 1:
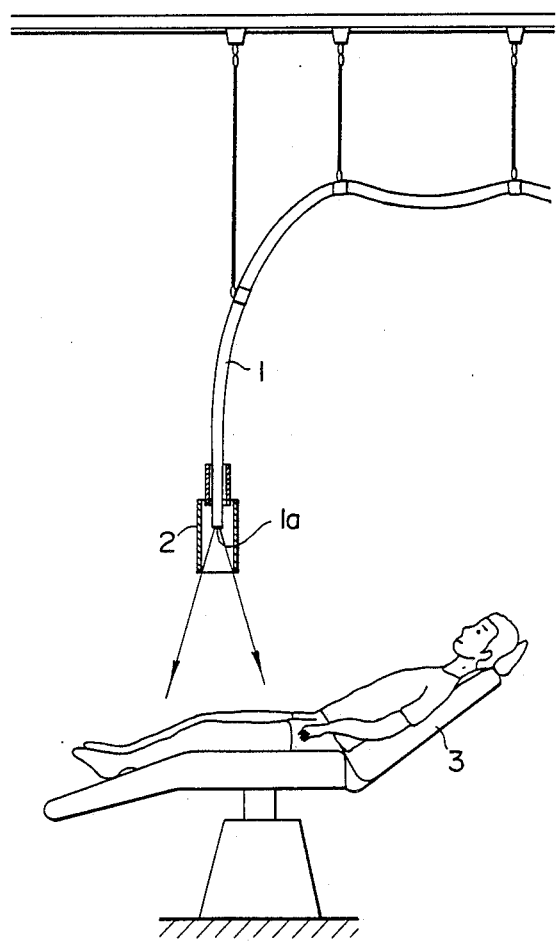
FIG. 1 is a view for explaining an embodiment of the light radiation device previously proposed by the present applicant for use in medical treatment.

FIG. 1 is a construction view for explaining an embodiment of the light radiation device for use in medical treatments as previously proposed by the present applicant In FIG. 1, numeral 1 designates a fiber optic cable for receiving sunlight or artificial light at its input end, not shown in FIG. 1, and transmitting the light therethrough The light to be transmitted through the fiber optic cable 1 is one that corresponds to visible-spectrum light obtainable in various ways previously proposed by the present applicant. In FIG. 1, numeral 2 designates a hood member installed at the light-emitting end portion 1a of the fiber optic cable and numeral 3 designates a chair for a patient. At the time of medical treatment, a patient is placed in the chair 3 and the visible-spectrum light thus transmitted through the fiber optic cable 1 is radiated onto the diseased part of a patient. As mentioned above, the light to be radiated onto the diseased part of the patient is the one that corresponds to the visible-spectrum components of the sunlight and free from the harmful elements such as ultraviolet and infrared rays. Consequently, it may be possible to give medical treatment safely with no fear of exposuring a patient to harmful ultraviolet and infrared rays. However, the above-mentioned light radiation device has such drawbacks that it is too large and too expensive to be used in a family setting.

Figure 2:
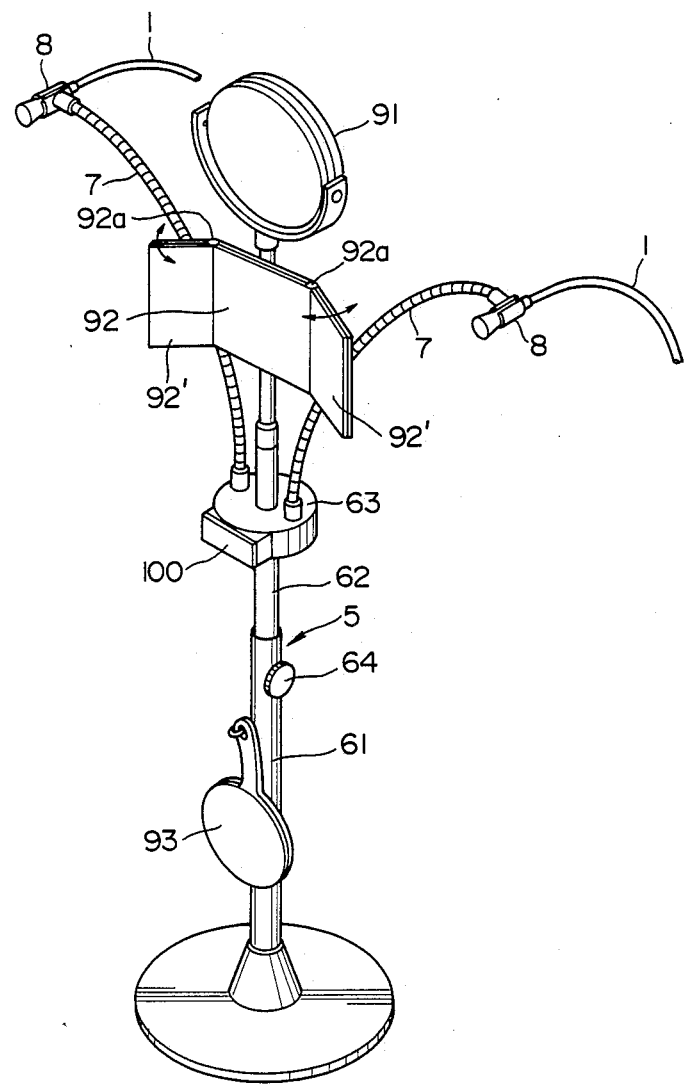
FIG. 2 is a perspective view for explaining an embodiment of a light radiation stand according to the present invention.

FIG. 2 is a perspective view for explaining an embodiment of a light radiation stand according to the present invention. In FIG. 2, numeral 1 designates a fiber optic cable for transmitting therethrough solar rays collected by a solar ray collecting device not shown in FIG. 2 and numeral 5 indicates a light radiation stand according to the present invention. The stand comprises a stand base, which is composed of a lower supporting pipe 61, an upper supporting pipe 62 and an supporting base 63, one or more deformable flexible conduits 7 vertically installed at the supporting base 63, a holding means 8 secured at the top of each conduit 7 so as to removably hold therein the light emitting end of the fiber optic cable 1, a mirror 91 having a convex surface at its one side and a concave surface at its another side, a three-side mirror 92, a hand mirror 93, a timer 100 and etc.

The light emitting end of the fiber optic cable 1 is usually supported by the holdering means 8 and, when light radiation is conducted, it is removed and used by hand or it is not removed and used in the state as supported by the holding means. In case when the cable 1 is used as supported by the holding means 8, its light-emitting end is easily directed in any desired direction bY bending the conduit 7 which being capable of to be freely bent and kept in the bent state. When the stand is not used for long period, it can be stored at any desired place of a small area, since the cable can be removed from it. In particular, the stand of the present invention is provided with the mirrors 91 and 93 which make it possible to observe the state of solar ray radiation onto a diseased part or other portion. The mirror 91 makes it possible to observe a whole radiation area at its convex surface and also to obtain a partly enlarged image at its concave surface in such a manner as mentioned after. The mirror 91 is reversively supported by the conduit so as to change over the observed area by turning over the mirror surface from its convex side to concave side or reverse, namely, to obtain the whole image at the convex mirror surface or a partly enlarged image at the concave mirror surface. The three-side mirror 92, which is a well known mirror having a mirror surface 92' being rotatable around an axis 92a, makes it easier to observe the sides of the patient's head and also makes it possible to observe the back of the patient's head when said mirror is used in combination with the hand mirror 93. Furthermore, the stand proposed by the present invention has the timer 100 in the supporting base 63 provided with a clock indication and a stop watch function. Radiation starting time can be easily read on the clock by pushing a start button. Furthermore, it is also possible to preset by the timer the radiating time in accordance with the such conditions as a state of disease, patient body's part to be radiated, sunlight intensity and so on. The light radiation stand 5 is supported by the lower supporting pipe 61 and the upper supporting pipe 62: the latter is slidably inserted into the former and firmly fixed at the desired length by the use of a knob 64. This feature makes it possible to adjust the level of the supporting base 63 to be most suitable for operator's height and state and body part to be radiated.

Figure 3:
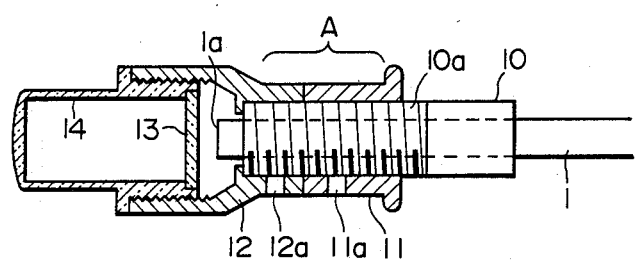
FIG. 3 is a detailed view of an light emitting end of a fiber optic cable.

FIG. 3 is a view for explaining an embodiment of a front (light-emitting) end of the fiber optic cable 1 shown in FIG. 2. In FIG. 3, numeral 1 designates a fiber optic cable, 1a a light-emitting end of said cable, 10 an armour placed onto the light-emitting end of the fiber optic cable 1, 11 a nut, 12 a connector, 13 a heat-reflecting filter and 14 a transparent safety cap.

The nut 11 and the connector 12 are screwed onto a threaded part formed on the external circumferential portion of the armour 10, as shown in FIG. 3, and then they are firmly secured at said cable end armour bY tightening them with use of special tools fitted into holes 11a and 12a specially bored into the nut 11 and the connector 12 respectively in such a way that the nut 11 and the connector 12 firmly secured opposite to each other on the end portion of the fiber optic cable 1. After the nut 11 and the connector 12 having being fixed thereon, both of them can not be detached from the fiber optic cable 1 without using the afore-mentioned special tools and thereby the safety connection can be guaranteed. In such a way, after fixing the connector 12 at the end of the fiber optic cable 1, the transparent protecting cap 14 is attached to the connector 12 through the heat-reflecting filter 13 as the occasion demands. The light emitted from the front end 1a of the fiber optic cable 1 are radiated through the transparent cap 14.

Figure 4:
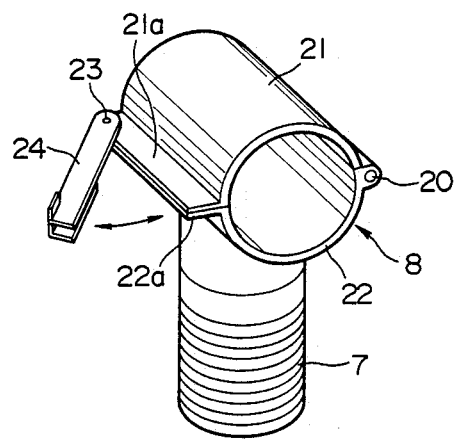
FIG. 4 is a detailed view for explaining an example of a holding means for holding the fiber optic cable.
Figure 5A:
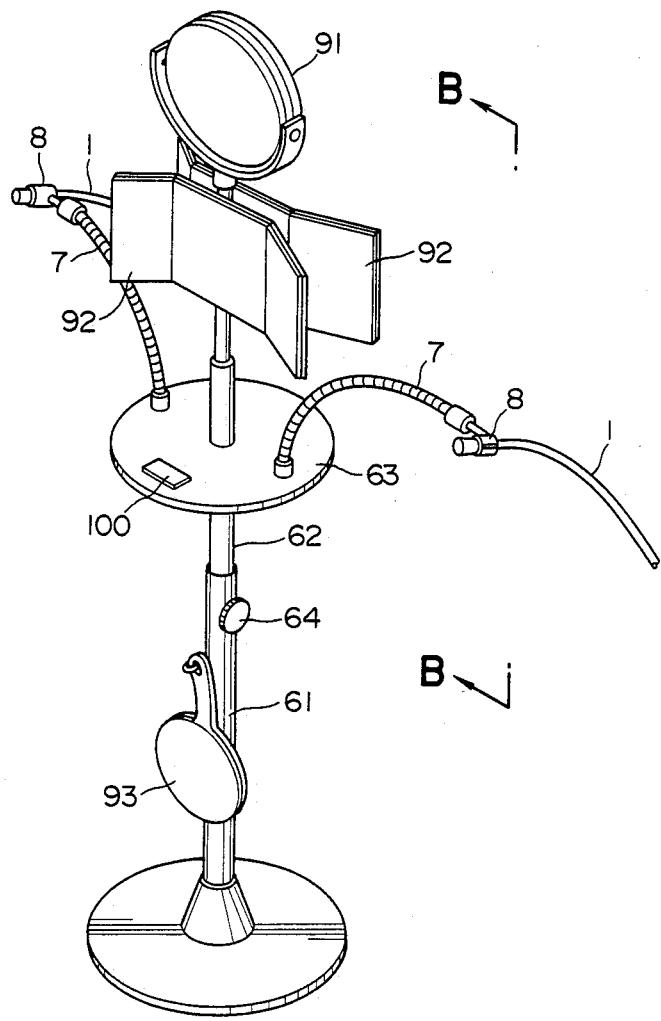
FIGS. 5(a)-5(d) are view for explaining another embodiment of the light radiation stand according to the present invention.
Figure 5B:
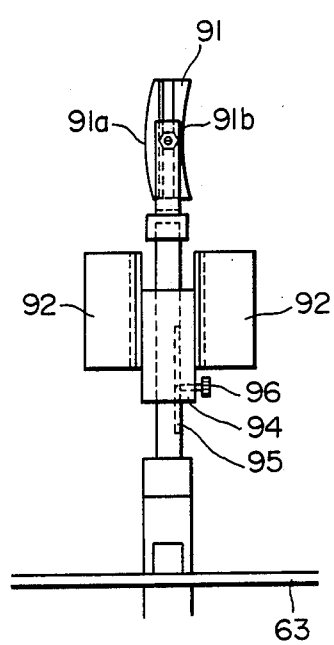
Figure 5C:
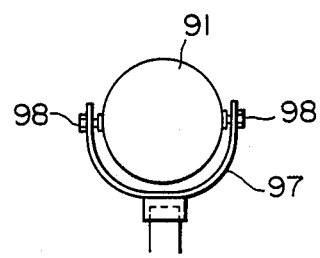
Figure 5D:
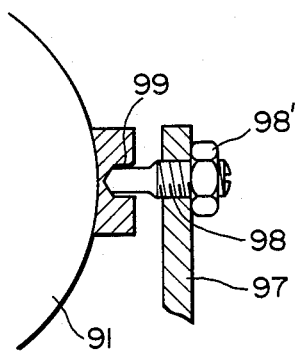

FIG. 4 shows an embodiment of the fiber optic cable holding means 8 illustrated in FIG. 2. Said holding means 8 comprises two semi-cylindrical bodies 21 and 22 being capable of rotating around a hinge pin 20 and an U-shape clamping member 24 which is mounted to either one of flat flanges 21a and 22a of the semi-cylindrical bodies in such a way that the clamping member 24 can rotate around a pin 23.

As is well known, both of the semi-cylindrical bodies 21 and 22 are opened by rotating them around the hinge pin 20.

The end portion A of the fiber optic cable 1 having the connector 12 firmly fixed thereto, as mentioned before, is inserted into the cylindrical portion formed with semi-cylindrical bodies 21 and 22, and then the bodies 21 and 22 are closed and the clamping member 24 is rotated around the pin 23 to nippingly held the both bodies' flat flanges 21a and 22a in its U-shape portion. In such a way, the front end portion of the fiber optic cable 1 is detachably supported by the holding means 8.

FIG. 5 is a view for explaining another embodiment of the light radiation stand according to the present invention.

FIG. 5 (a) is an entire perspective view of the light radiation stand.

FIG. 5 (b) is a side view of a head portion taken on line B—B of FIG. 2.

FIGS. 5 (c) and (d) are views for explaining a mirror 91 in detail.

In FIGS. 5 (a)–5(d), parts similar to those shown in FIG. 2 are denoted by the same reference numerals.

In this embodiment, the light radiation stand is capable of radiating light onto two persons at the same time by using two fiber optic cables placed at two cable-end holders and two pieces of three-side mirrors 92 mounted facing in opposite direction each other.

As shown in FIG. 5 (b), the three-side mirrors 92, as being placed back to back each other, are supported by a supporting member 94 which can be adjusted for its level and secured on a supporting pipe by screwing a set screw 96 into a groove 95 provided on said pipe. A mirror 91, as stated above, has a convex mirror at one side and a concave mirror at another side and pivotally supported by an arm 97 as illustrated in FIG. 5 (c). As shown in FIG. 5 (d), the mirror 91 is supported by means of two supporting bolts in such a way that they are screwed into through holes from both sides of arm 97 and fitted into the corresponding receiving holes 98 of both side rests of the mirror. Each bolt has a tapered tip end corresponding to the form of receiving hole 99 of the mirror side rests. Therefore, by adequately tightening the two bolts 98 at both sides of the support arm 97 the mirror can be fixed by the action of friction force created by the bolts' tips in the receiving holes 99 of the mirror. Since the mirror can be rotated by applying a force overcoming the bolts' friction force, it is possible to easily adjust the tilting angle of the mirror 91 without loosening the bolts. The bolts 98 can be provided with a locknut to prevent them from rotating at the time of adjustment of the mirror 91.

Figure 6:
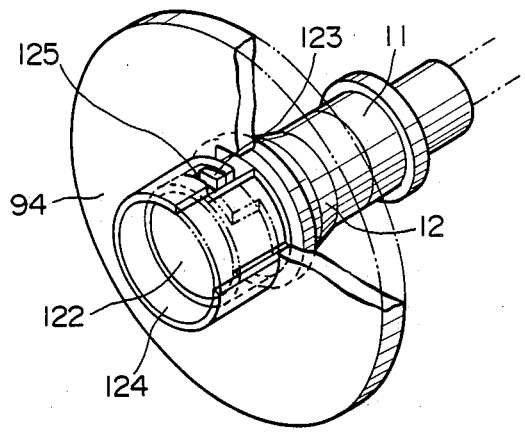
FIGS. 6-9 are view for explaining an another embodiment of the light radiation stand having a mirror secured at a near to tip end of the fiber optic cable.
Figure 6:
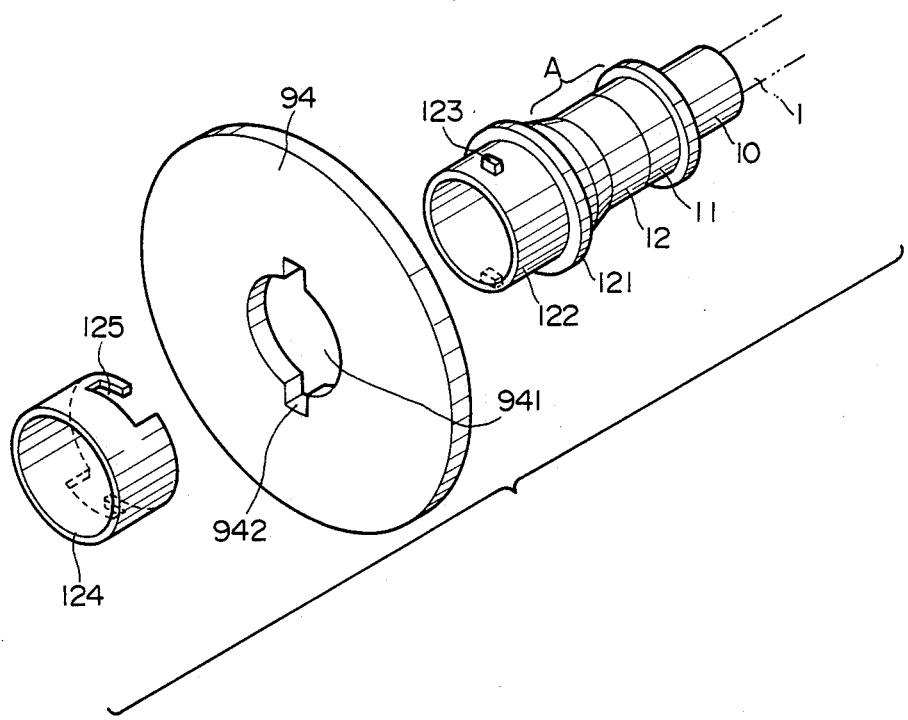

FIGS. 6–9 illustrate further embodiments of the light radiation stands having a mirror placed near the light emitting end of a fiber optic cable. Such construction makes it easier to observe the diseased part to be radiated. Furthermore, application of the light emitting end provided with a mirror in combination with a mirror 91, a three-side mirror and a hand mirror gives the possibilitY to carry out the light radiation with easy observation on the part whereto the eye could not reach. Each embodiment will be explained as follows:

Referring to FIG. 6, there is shown an embodiment making it possible to removably attach a mirror to a connector 12 shown in FIG. 3. FIG. 6 (a) is a partially cutaway view in perspective of the connector portion with a mirror mounted thereon and FIG. 6 (b) is a disassembled view of the portion shown in FIG. 6 (a). In FIGS., numeral 94 designates a mirror and numeral 124 designates a fixing member. A collar 121 is provided at the middle part of the connector 12 and two projections 123 are arranged oppositely at the same diametral line on the fitting portion 122 ahead of the collar 122. The mirror 94 has a hole with diameter corresponding to the outer diameter of the connector's fitting portion 122. The hole 941 is made with two notches 942 corresponding to the above-mentioned projections. The fixing member 124 also has two symmetrically located L-notches. The mirror 94 is mounted on the connector in the following manner:

A nut 11 and a connector 12 are screwed onto an armour 10 wherein a light emitting end of a fiber optic cable 1 is fixed.

The mirror 94 is mounted with its backside first on the fitting portion 122 of the connector 12 and pushed against the connector's stop collar 121 by aligning the mirror side notches 942 with connector side projections 123. The fixing member 124 is then fitted onto the connector front end projecting from the mirror's front side in such a way as to engage its notches 125 with the projections 123 on the connector fitting portion 122. The fixing member is rotated in clock-wise direction to clasp the mirror between the fixing member and the connector collar. Disassembling the mirror can be done by reversing the above-mentioned procedure. The construction and the procedure for mounting/dismounting the mirror on/from the connector holding the fiber optic cable is described above. Since no affection of attaching the mirror to the portion A of the connector 12 is obtained, the holding means 8 with a mirror shown in FIGS. 2 and 3 can be mounted to said portion of the connector.

In this embodiment, the fixing portion 124 serves as a protecting cap and therefore the cap 14 illustrated in FIG. 3 may be omitted.

Figure 7:
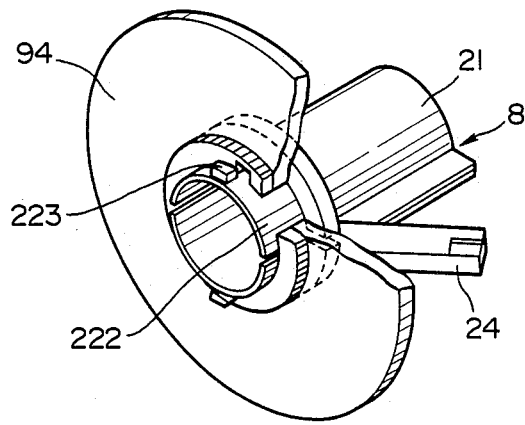
Figure 7:
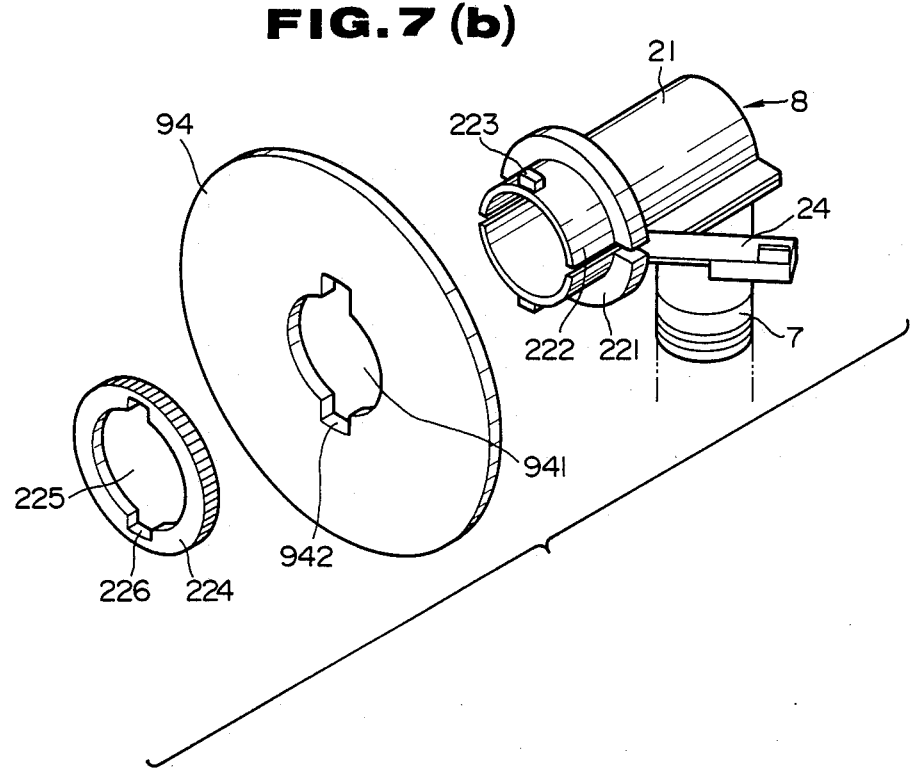

Referring to FIG. 7, there is shown an embodiment allowing for removably attaching a mirror to a holding means 8 illustrated in FIG. 3. FIG. 7 (a) is a partially cutaway view in perspective of the holding portion with a mirror mounted thereon and FIG. 7 (b) is a disassembled view of the portion shown in FIG. 7 (a) In FIGS., numeral 94 indicates a mirror and numeral 224 indicates a fixing ring. A split collar 22 is provided at the middle part of a split holder 8. Two projections 123 are positioned oppositely at the same diametral line on the front fitting portion 222 ahead of the collar 221. The mirror 94 has a fitting hole 941 and two notches 942 which are similar to those of the mirror shown in FIG. 6. The fixing ring 224 has a notched outer ring surface and also has a hole 225 with two notches 226 which are the same in shape and size as those of the mirror 94.

The mirror 94 is mounted on the connector in the following manner:

A clamp 24 of the split holder 8 is opened, the holder's upper half 21 is rotated to open and the connector's portion A wherein the light emitting end of the fiber optic cable is secured is placed in the holder's lower half, then the upper half is closed and the clamp 24 is engaged to secure the cable end in the holder 8 attached to the top of a conduit 7. The mirror 94 is placed with its backside first on the fitting portion 222 of the holder 8 and pushed against the collar 221. The fixing ring 224 is then fitted onto the connector front end projecting from the mirror's front side in such a way as to engage its notches 226 with the projections 223 on the holder's fitting portion 222.

The fixing ring 224 is rotated in required direction to secure the mirror 94 between the fixing ring 224 and the holder's collar 221.

Disassembling the mirror can be done by reversing the above-mentioned procedure.

In this embodiment, the mirror 94 is securely mounted on the holder fixed to the top of the conduit 7.

Figure 8:
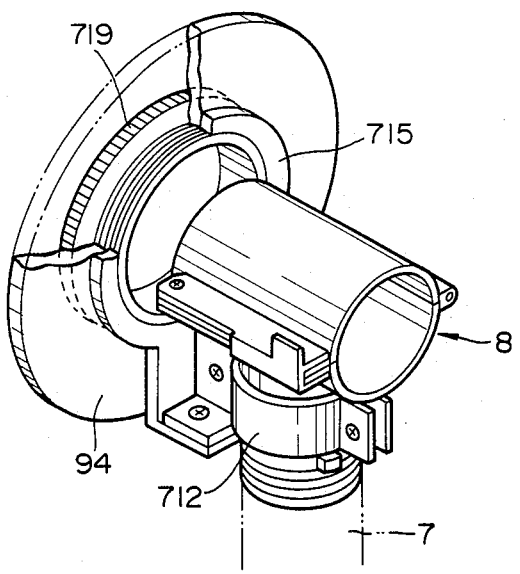
Figure 8:
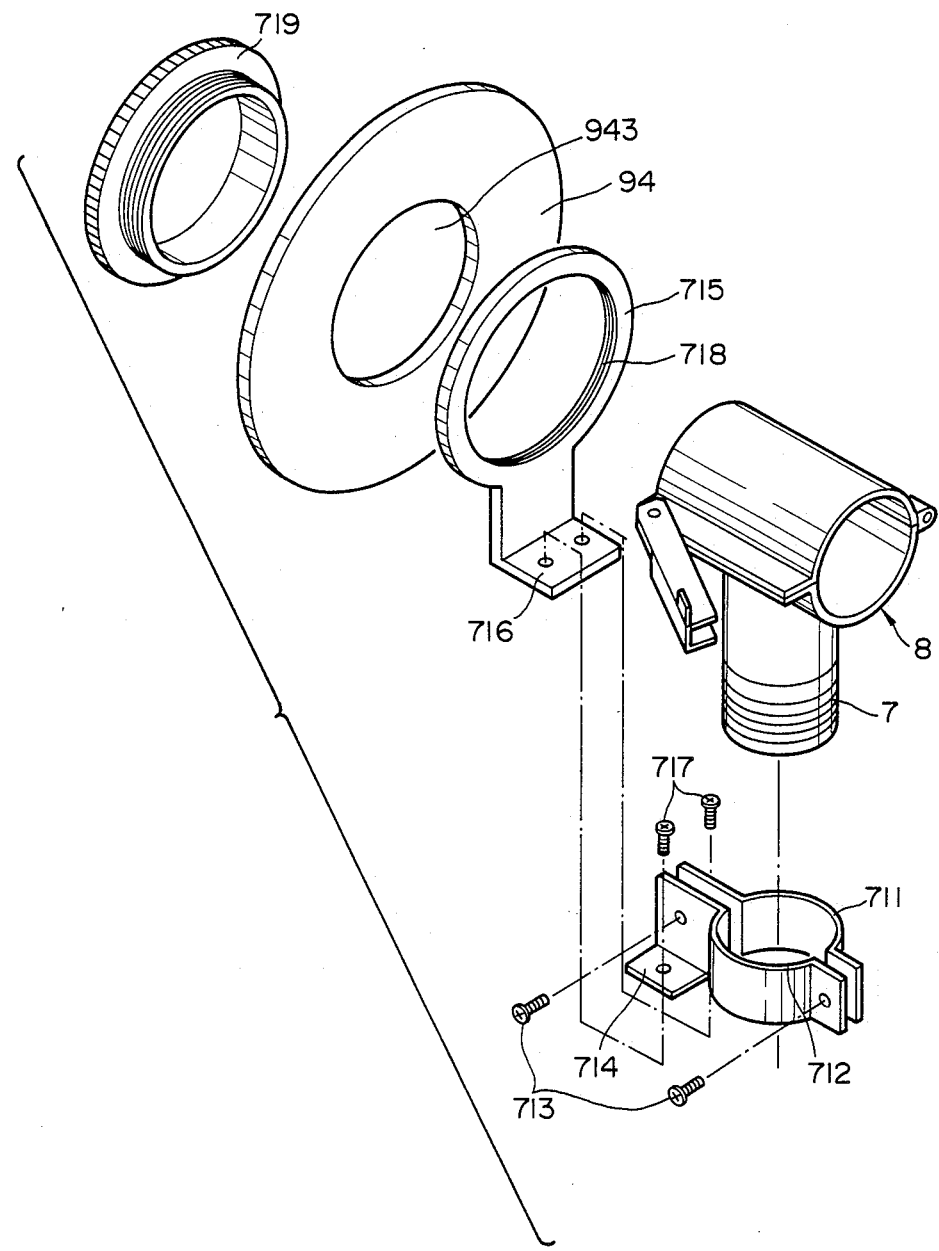

FIG. 8 shows an embodiment enabling to removably secure a mirror onto a conduit 7.

FIG. 8 (a) is a partially cutaway viww in perspective back side of the conduit with a mirror mounted thereon.

FIG. 8 (b) is a disassembled view of the portion shown in FIG. 8 (a). In FIGS., 94 is a mirror, 7 is a conduit, 8 is a holding means, 711–719 are members for fixing the mirror, namely, including fixing bands 711, 712, supporting block 715 and clamp ring 719.

The mirror 94 is mounted on the conduit 7 in the following way:

At the upper part of the conduit 7 the halves of split fixing band 711 and 712 are fixed by threadedly connecting their flanges at both sides by the use of flange screws 713. A footplate 715 of the supporting block 715 is placed under the bent plates 714 at the front side flange of the fixing band's halves 711 and 712 so as to be connected with each other by tightening screws 717 into the matched holes in both plates. When the supporting block 715 is attached on the upper part of the conduit 7, it is desirable to align the axis of the block with axis of the holder 8.

The mirror 94 has a center hole 943 of diameter slightly larger than the threaded hole 718 in the supporting block 718. The mirror 94 is mounted with its backside first on the supporting block in such a way as to align the axes of their holes 943 and 781, and then it is secured by screwing threaded portion of the clamping ring 719 into the threaded hole 718 of the supporting block so as to firmly secure the mirror 94. The mirror can be removed by reversing the above-mentioned procedure. The supporting block 715 may be always attached to the conduit 7 by the use of the fixing band halves 711 and 712. This embodiment not only assures the high durability of fixing the mirror but also make it possible to remove and mount the mirror without removing the fiber optic cable from the holder 8 or to remove and attach the cable without removing the mirror 94.

Figure 9A:
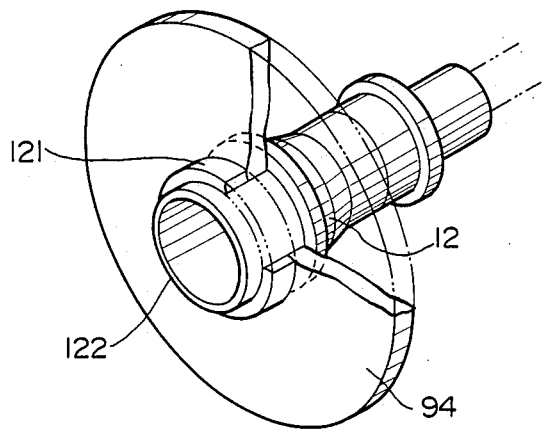
Figure 9B:
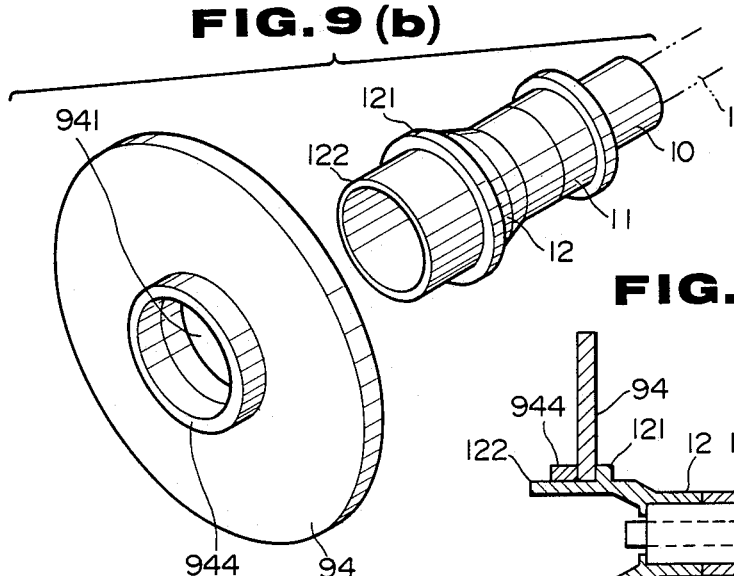
Figure 9C:
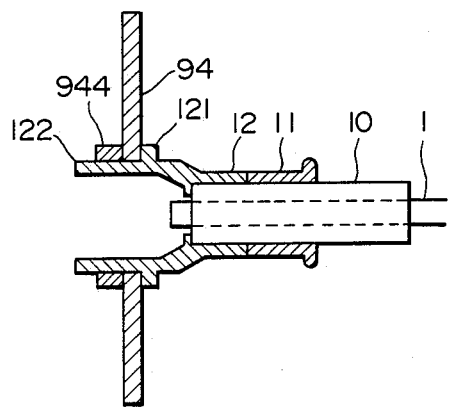

Referring to FIG. 9, there is shown an embodiment allowing for easily attaching/removing the mirror to/from the above-mentioned connector.

FIG. 9 (a) is a partially cutaway view in perspective of the connector portion with a mirror mounted thereon and FIGS. 9 (b) and (c) are respectively a disassembled view and a cross-sectional view of the portion shown in FIG. 9 (a).

In FIGS., numeral 12 designates a connector and numeral 94 designates a mirror. The connector 12 is similar to that shown in FIG. 6 (b), but does not have the fitting projection 123. The mirror 94 has a flange 44 with the same inner diameter as that of its fitting hole. The diameter of the mirror's fitting hole 941 is the same as the outer diameter of the connector's fitting part 122. Consequently, in this embodiment the mirror 94 can be easily mounted on the connector 12 by pushing the mirror by aligning its hole axis with the connector fitting portion's axis.

Figure 10:
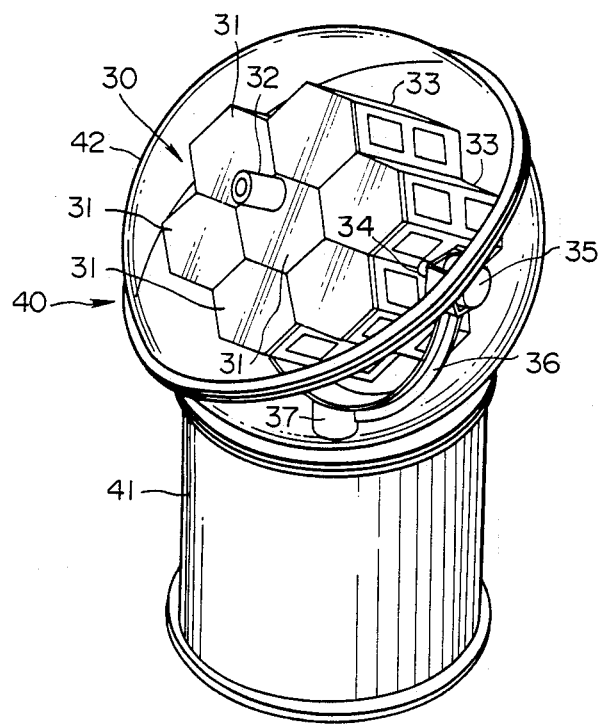
FIG. 10 is a view for explaining an example of a solar ray collecting device to be used in the embodiment of the present invention.

FIG. 10 is an entire perspective view illustrating, by way of example, a solar ray collecting device for guiding the sunlight into the afore-mentioned fiber optic cable 1. In FIG. 10, a capsule 40 for use in the solar ray collecting device is constructed of a cylindrical body 41 and a transparent dome-shaped head 42. As shown in FIG. 10, the solar ray collecting device 30 is accommodated in the capsule 40 when the device is being used. The solar ray collecting device 30 comprises one lens, several lenses or possibly large number of lenses 31, a solar position sensor 32 for detecting the sun's location, a support frame body 33 for integrally holding the lens 31 and the sensor 32, a first-revolution shaft 34 for rotating the support frame 33, a first-motor 35 for rotating the first revolution shaft 34, a support arm 46 for supporting the lens 31 or the motor 35, a second-revolution shaft 37 installed so as to intersect the first revolution shaft 34 perpendicularly thereto, and a second-motor, not shown in FIG. 10, for rotating the second revolution shaft 37. The direction of the sun is detected by means of the solar position sensor 32 and its detection signal controls the first and second motors so as to always direct the lens 31 toward the sun, and the sunlight focused by the lens 31 is guided into the fiber optic cable, not shown in FIG. 10 (that is, into an end, not shown in FIG. 2, of the fiber optic cable shown in FIG. 2) through its end surface set at the focal point of the lens. The guided sunlight is transmitted through the fiber optic cable to anywhere the light is needed.

Concerning the above-mentioned solar ray collecting device, several types of devices, which may have respectively one lens, several (2 or 4) lenses or a large number of lenses (for instance, 7, 19, 61, about 200 or about 1600 lenses) depending upon the purpose of their use, have been proposed by the inventor.

Figure 11:
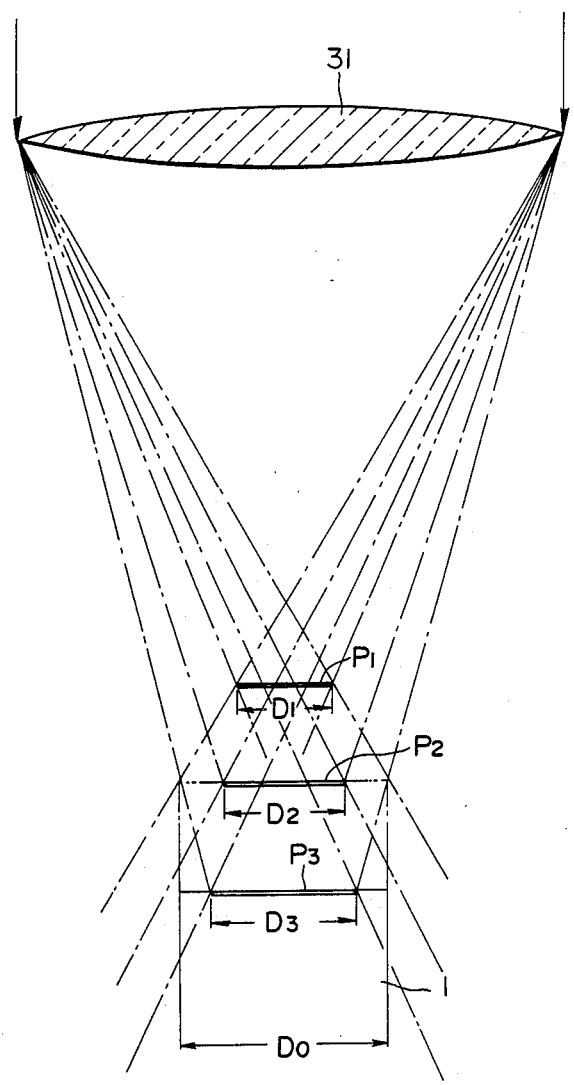
FIG. 11 is a view for explaining an example of guiding solar raYs into a light receiving end of the fiber optic cable.

FIG. 11 is a view for explaining how to guide the light rays corresponding to the visible-spectrum components of the sunlight into a fiber optic cable 1. In FIG. 11, 31 is a lens system consisting of a Fresnel lens or the like, and the sunlight focused by the lens system 31 is guided into a fiber optic cable 1 as mentioned before. In case of focusing the sunlight through the lens system, the solar image has a central portion consisting of almost white light and a circumferential portion containing therein a large amount of light components of the wavelengths corresponding to focal point of the lens system. Namely, in the case of focusing the sunlight through the lens sYstem, the focal point and the size of the solar image will vary in accordance with the component wavelengths of the light. For instance, the blue color light having a short wavelength makes a solar image of diameter D1 at a position P1. Furthermore, the green color light makes a solar image of diameter D2 at a position P2 and the red color light makes a solar image of diameter D3 at a position P3. Consequently, as shown in FIG. 10, when the light-receiving end-surface of the fiber optic cable 1 is set at the position P1, it is possible to collect the sunlight containing plenty of the blue color components at the circumferential portion thereof. When the light-receiving end-surface of the fiber optic cable 1 is set at the position P2, it is possible to collect the sunlight containing plenty of the green color components at the circumferential portion thereof. When the light-receiving end-surface of the fiber optic cable 1 is set at the position P3 it is possible to collect the sunlight containing plenty of the red color components at the circumferential portion thereof. In each case, the diameter of the fiber optic cable can be selected in accordance with the light ray components to be collected. For instance, the required diameters of the fiber optic cables are D1, D2 and D3, respectively, depending on the colors of the light rays to be stressed, i.e. the blue, green and red colors. In such a way, the required amount of the fiber optic cable can be saved and thereby the sunlight containing therein plenty of desired color components can be collected most effectively and further, as shown in FIG. 11, if the diameter of the light-receiving end of the fiber optic cable 1 is enlarged to D0, it may be possible to collect visible light containing therein all of its wavelength components.

As is apparent from the foregoing description, according to the present invention, it may be possible to provide a light radiation device, which is low cost, portable, compact and very easy to operate, allowing for observing radiating state by means of a mirror and, furthermore, to preset by the timer a irradiating period required in accordance with the state of disease, light intensity and other conditions concerned.

I claim:

1. A light radiation stand for holding a light emitting end of a light-transmitting fiber optic cable, characterized in that said light radiation stand comprises a stand base, one or more deformable flexible conduits vertically installed on the upper part of said base, a fiber optic cable holding means mounted on the tip end portion of each conduit and a mirror integrally mounted to the base.

2. A light radiation stand according to the claim 1, characterized in that said base comprises a vertical shaft and the mirror is rotatably attached to said shaft.

3. A light radiation stand according to the claim 2, characterized in that the mirror is rotatably attached to a horizontal axis at an upper part of the shaft.

4. A light radiation stand according to the claim 1, characterized in that said base comprises a vertical shaft and the mirror is rotatably attached to a horizontal axis at the upper part of the shaft.

5. A light radiation stand according to the claim 1 or claim 4, characterized in that the mirror has a convex surface at its one side and a concave surface at its another side.

6. A light radiation stand according to the claim 1 or claim 4, characterized in that the mirror is a three-side mirror, 7. A light radiation stand according to the claim 1, characterized in that the mirror is removably attached to a fiber optic cable holding means.

8. A light radiation stand according to the claim 1, characterized in that the mirror is removably attached to an end of the fiber optic cable.

9. A light radiation stand according to the claim 1 or claim 8, characterized in that a timer is integrally mounted in the base.

* * * * *